United States Patent [19]

Hayashi et al.

[11] Patent Number: 4,946,862
[45] Date of Patent: Aug. 7, 1990

[54] THIOPHENE DERIVATIVE AND PROCESS FOR PREPARING THE SAME

[75] Inventors: Kimiaki Hayashi, Suita; Yasuhiko Ozaki, Neyagawa; Kenji Yamada, Saitama; Hideyuki Takenaga, Urawa; Ichizo Inoue, Kawanishi, all of Japan

[73] Assignee: Tanabe Seiyaku Co., Ltd., Osaka, Japan

[21] Appl. No.: 215,775

[22] Filed: Jul. 6, 1988

[30] Foreign Application Priority Data

Jul. 9, 1987 [JP] Japan .................... 62-171669

[51] Int. Cl.$^5$ .................... C07D 333/20; A61K 31/38
[52] U.S. Cl. ........................ 514/438; 549/74
[58] Field of Search ............... 549/74, 75; 514/438

[56] References Cited

U.S. PATENT DOCUMENTS 3,109,845  10/1963  Seeger .
4,128,561  12/1978  Braye ........................ 549/74

FOREIGN PATENT DOCUMENTS 1344455  10/1962  France .
55-16416  5/1980  Japan .

OTHER PUBLICATIONS

Hideyuki Takenaga et al; "Effects of Trimebutine Maleate (TM-906) on the Spontaneous Contraction of Isolated Guinea Pig Colon", Japan. J. Pharmacol. 34, 177–181 (1984).

Tanabe, Seiyaku Co., Ltd., Chemical Abstracts, vol. 99, No. 21, p. 587, No. 175393b (1983).

Furukawa et al., Chemical Abstracts, vol. 101, No. 13, p. 44, No. 103859v (1984).

European Search Report, Apln. No. 88306119.4–, Tanabe Seiyaku Co., Ltd., Oct. 24, 1988.

Primary Examiner—Alan Siegel
Attorney, Agent, or Firm—Birch, Stewart, Kolasch & Birch

[57] ABSTRACT

A thiophene derivative of the formula:

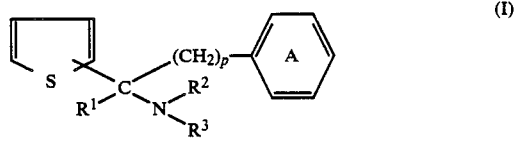

wherein $R^1$, $R^2$ and $R^3$ are a lower alkyl group, Ring A is a substituted or unsubstituted phenyl group and p is an integer of 1 to 3, or a salt thereof and processes for preparing the same are disclosed. The thiophene derivative (I) is useful as the regulator of gastrointestinal tract motility.

6 Claims, No Drawings

THIOPHENE DERIVATIVE AND PROCESS FOR PREPARING THE SAME

This invention relates to a thiophene derivative and processes for preparing the same. More particularly, it relates to a novel thiophene derivative of the formula:

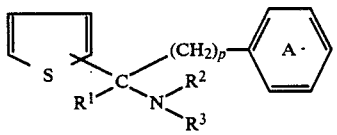

wherein $R^1$, $R^2$ and $R^3$ are a lower alkyl group, Ring A is a substituted or unsubstituted phenyl group and p is an integer of 1 to 3, or a salt thereof.

It is known that trimebutine maleate (chemical name: 2-dimethylamino-2-phenylbutyl 3,4,5-trimethoxybenzoate maleate) is useful as the regulator of gastrointestinal tract motility (cf. Japan. J. Pharmacol. Vol. 34, pp 177–181(1984)).

As a result of various investigations, we have now found that the thiophene derivative (I) and a salt thereof have a potent regulating effect on the motility of gastrointestinal tracts.

Examples of the compounds of the present invention include those of formula (I) in which $R^1$, $R^2$ and $R^3$ are a lower alkyl group such as methyl, ethyl, propyl or butyl, Ring A is a phenyl group or a phenyl group having to three substituents selected from the group consisting of a lower alkoxy group such as methoxy, ethoxy, propoxy or butoxy, a halogen atom such as fluorine, chlorine or bromine and a hydroxy group, and p is 1, 2 or 3.

Among the compounds of the present invention, a preferred subgenus are those of the formula (I) in which $R^1$ is an ethyl group, $R^2$ and $R^3$ are methyl groups, Ring A is a phenyl group or a phenyl group having one to three substituents selected from the group consisting of a methoxy group, a chlorine atom and a hydroxy group, and p is 1 or 3.

Further preferred subgenuses are those of formula (I) in which $R^1$ is ethyl group, $R^2$ and $R^3$ are methyl groups, Ring A is a phenyl group, a 3,4-dimethoxyphenyl group, a 3,4,5-trimethoxyphenyl group or a 4-chlorophenyl group, and p is 1 or 3.

While the compound (I) of the present invention can exist in the form of two optical isomers due to the asymmetric carbon atom involved therein, the present invention includes both of such optical isomers and a racemic modification thereof.

According to the present invention, the compound (I) can be prepared by, for example, alkylating an amine compound of the formula:

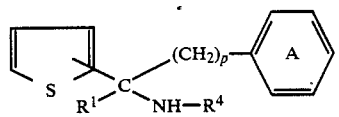

wherein $R^4$ is a hydrogen atom or a lower alkyl group, and $R^1$, Ring A and p are the same as defined above.

The alkylation of the amine compound (II) can be carried out by reacting the compound (II) with an aldehyde compound of the formula:

RCHO wherein R is hydrogen or a lower alkyl group having a number of carbon atoms less than that of $R^2$ (or $R^3$) by one carbon atom, in the presence of a reducing agent. Examples of the reducing agents include sodium cyanoborohydride, sodium borohydride, formic acid, sodium formate and the like. It is preferred to carry out the reaction in a solvent (e.g., alkanol, acetonitrile) or without a solvent, at a temperature of −10° to 120° C., especially preferred bring 10° to 100° C.

The alkylation of the compound (II) can also be carried out by reacting the compound (II) with an alkyl halide (e.g., methyl iodide, ethyl iodide). It is preferred to carry out the reaction in a suitable solvent (e.g., dimethylformamide, hexamethylphosporic triamide, ethyl acetate, acetonitrile) in the presence of an acid acceptor (e.g., potassium carbonate, sodium bicarbonate) at a temperature of 0° to 90° C. When the thus-obtained compound (I) is a compound in which the Ring A is a 3,4,5-tri(lower alkoxy)phenyl group, if required, said compound may be subjected to dealkylation to give the compound (I) in which the Ring A is a 4-hydroxy-3,5-di(lower alkoxy)phenyl group. The dealkylation can be carried out by treating the trialkoxyphenyl-compound (I) with thiocresol, sodium hydride or hexamethylphosphoric triamide. It is preferred to carry out the reaction in a solvent (e.g., toluene, xylene) at a temperature of 20° to 150° C., especially preferred being 90° to 130° C.

When the thus-obtained compound (I) is a racemic modification, said racemic modification can be optically resolved in a traditional manner. The optical resolution can be carried out, for example, by reacting the racemic modification of the compound (I) with a resolving agent in a solvent to form two kinds of diastereoisomeric salts, then isolating the crystals of a less soluble diastereoisomeric salt by utilizing the difference in solubility of two diastereoisomeric salts, further isolating the more soluble diastereoisomeric salt from the mother liquor, and cleaving each of the thus-obtained diastereoisomeric salts.

The compound (I) obtained in the above-mentioned reactions can be readily converted into a salt thereof in a traditional manner, for example, by treating with an acid in a solvent.

As mentioned hereinbefore, the compound (I) and its salt have a potent regulating effect on the motility of gastrointestinal tracts and are especially characterized by a potent excitatory effect on the gastrointestinal tract in conditions of depressed activity. Moreover, some of the compounds (I) are characterized in that they show dual effects on the gastrointestinal tract motility, i.e., excitatory effect on the gastrointestinal tract in conditions of depressed activity and inhibitory effect on the gastrointestinal tract in conditions of hyperactivity. Further, the compounds (I) and their salts are also characterized in that they are low in toxicity and therefore have great safety as a medicament. Therefore, the compounds (I) and their salts are useful as a regulator of gastrointestinal tract motility in a warm-blooded animals including human beings. For example, they can be used for the improvement, treatment and/or prophylaxis of gastrointestinal symptoms (e.g., abdominal pain, nausea, abdominal distention) in chronic gastritis, irritable bowel syndrome and the like. The compounds (I) of the present invention can be used for pharmaceutical use either in the free form or in the form of a pharmaceutically acceptable salt thereof. Examples of these salt of the compounds (I) include inorganic acid addition salts such as hydrochloride, hydrobromide, sulfate or phosphate, and organic acid addition salts such as succinate, maleate, fumarate or tartarate.

The compounds (I) or a salt thereof can be administered either orally or parenterally (e.g., intravenously, intramuscularly, intradermally) and used in the form of a pharmaceutical preparation which may contain a pharmaceutical carrier suitable for oral or parenteral administration. The pharmaceutical preparation may be in the solid form such as tablets, granules or capsules or in the liquid form such as solutions, suspensions or emulsions. They may be sterilized and/or may contain auxiliaries such as stabilizing, wetting or emulsifying agents.

The dose of a compound (I) or a pharmaceutically acceptable salt thereof may vary over a wide range depending on the administration route, the age, body weight or conditions of patients and severity of diseases, and the like, but is usually in the range of 0.001 to 50 mg/kg/day. In case of oral administration, said dose is especially in the range of 1 to 20 mg/kg/day.

Concomitantly, the starting compound (II) of the present invention can be prepared, for example, by the steps of:

(i) reacting a compound of the formula:

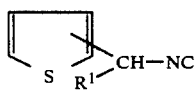
(III)

wherein $R^1$ is the same as defined above, with a compound of the formula:

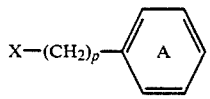
(IV)

wherein X is a halogen atom and Ring A and p are the same as defined above, in the presence of an acid acceptor (e.g., lithium diisopropylamide) to give a compound of the formula:

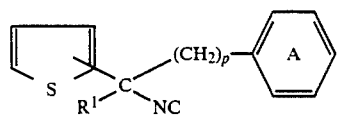
(V)

wherein $R^1$, Ring A and p are the same as defined above, (ii) treating the compound (V) with an acid (e.g., hydrochloric acid) in a solvent to give a compound of the formula:

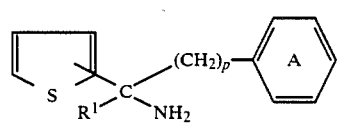
(II-A)

wherein $R^1$, Ring A and p are the same as defined above, and, (iii) if required, further alkylating the compound (II-A) to give a compound of the formula:

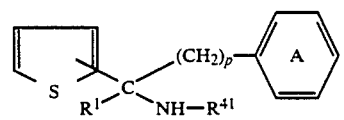
(II-B)

wherein $R^{41}$ is a lower alkyl group, and $R^1$, Ring A and p are the same as defined above. Besides, the compound (II) in which $R^4$ is methyl group can also be prepared by treating the compound (V) with a reducing agent (e.g., lithium aluminum hydride) in a solvent.

Throughout to the specification and claims, the terms "lower alkyl" and "lower alkoxy" should be interpreted as reffering to alkyl having one to 4 carbon atoms and alkoxy having one to 4 carbon atoms, respectively.

EXAMPLE 1

(1) A solution of 2 g of diisopropylamine in 10 ml of tetrahydrofuran is cooled at $-60°$ C and 10 ml of 1.6 M n-butyl lithium in hexane are added dropwise to the solution. The mixture is stirred at the same temperature for 30 minutes to give a solution of lithium diisopropylamide. A solution of 2 g of 1-(2-thienyl)propyl isocyanide in 10 ml of tetrahydrofuran is added dropwise at $-60°$ C. to the solution obtained above and the mixture is stirred at the same temperature for 30 minutes. A solution of 3.8 g of 3-(3,4,5-trimethoxyphenyl)propyl chloride in 5 ml of tetrahydrofuran is added dropwise to the mixture at the same temperature, and said mixture is stirred for 1 hour. The reaction mixture is neutralized with acetic acid, and ethyl acetate and water are added thereto. The organic layer is separated therefrom, washed with an aqueous saturated sodium chloride solution, dried and evaporated to remove solvent. The residue is purified by silica gel column chromatography (solvent; n-hexane:ethyl acetate=4:1) to give 3.4 g of 1-ethyl-4-(3,4,5-trimethoxyphenyl)-1-(2-thienyl)butyl isocyanide as a colorless oil. yield: 71.5%

(cm$^{-1}$): 2140, 1590

(2) A solution of 2.8 g of 1-ethyl-4-(3,4,5-trimethoxyphenyl)-1-(2-thienyl)butyl isocyanide in 10 ml of tetrahydrofuran is added dropwise to a suspension of 0.6 g of lithium aluminum hydride in 5 ml of tetrahydrofuran under ice-cooling and the mixture is stirred at room temperature for 16 hours. To the reaction mixture are added successively, 0.6 ml of water, 0.6 ml of an aqueous 15% sodium hydroxide solution and 1.8 ml of water, and the insoluble materials are removed by filtration. The filtrate is concentrated under reduced pressure and the residue is purified by silica gel column chromatography (solvent; chloroform:ethanol=20:1) to give 1.7 g of 1-ethyl-4-(3,4,5-trimethoxyphenyl)-1-(2-thienyl)-N-methylbutylamine as a colorless oil. yield:60%

(cm$^{-1}$): 3320, 1590

MS.(m/e): 363(M+)

(3) 1.7 g of 1-ethyl-4-(3,4,5-trimethoxyphenyl)-1-(2-thienyl)-N-methylbutylamine are dissolved in 15 ml of acetonitrile. 1.5 ml of 35% formalin and 0.59 g of sodium cyanoborohydride are added to the solution, and the mixture is adjusted to pH 6.5 with methanol containing hydrogen chloride and stirred at room temperature for 8 hours. After the reaction, the mixture is acidified with 10% hydrochloric acid and stirred for 30 minutes. The mixture is alkalized with an aqueous 20% potassium carbonate solution and concentrated under reduced pressure. The residue is extracted with ethyl acetate, and the extract is washed with an aqueous saturated sodium chloride solution, dried and evaporated to remove solvent. The residue is purified by silica gel column chromatography (solvent; chloroform:ethanol=30:1) to give 1.4 g of 1-ethyl-4-(3,4,5-trimethoxyphenyl)-1-(2-thienyl)-N,N-dimethylbutylamine as colorless crystals. yield; 79.3% M.p. 62°–63 ° C. (recrystallized from ether-n-hexane)

- ($cm^{-1}$): 2900, 1590

MS.(m/e): 348($M^+$—$C_2H_5$)

NMR($CDCl_3$)δ:0.82(t, 3H), 1.25–2.23(m, 6H), 2.06(s, 6H), 2.52(t, 2H), 3.82, 3.85(s,s, 9H), 6.40(s, 2H), 6.6–7.3(m, 3H)

EXAMPLE 2

(1) 6.0 g of 3-phenylpropyl chloride and 5.4 g of 12-thienyl)propyl isocyanide are treated in the same manner as described in Example 1-(1) to give 8.7 g of 1-ethyl-4-phenyl-1-(2-thienyl)butyl isocyanide as a colorless oil. yield; 90.6%

($cm^{-1}$): 2130

MS.(m/e): 269($M^+$), 240($M^+$—$C_2H_5$)

(2) 8.6 g of 1-ethyl-4-phenyl-1-(2-thienyl)butyl isocyanide are treated in the same manner as described in Example 1-(2) to give 4.4 g of 1-ethyl-4-phenyl-1-(2-thienyl)-N-methylbutylamine as a colorless oil. yield; 50.6%

($cm^{-1}$): 3320, 1590

MS.(m/e): 273($M^+$)

(3) 4.4 g of 1-ethyl-4-phenyl-1-(2-thienyl)-N-methylbutylamine are treated in the same manner as described in Example 1-(3) to give 3.7 g of 1-ethyl-4-phenyl-1-(2-thienyl)-N,N-dimethylbutylamine as a colorless oil. yield; 80%

MS.(m/e): 288($M^+$+1)

NMR($CDCl_3$)δ:0.80(t, 3H), 1.4–2.0(m, 6H), 2.09(s, 6H), 2.59(t, 2H), 6.6–7.2(m, 8H)

Maleate: colorless crystals

M.p. 119°–121° C. (recrystallized from ethyl acetate)

EXAMPLE 3

(1) 2.5 g of 1-(2-thienyl)propyl isocyanide and 4.4 g of 3,4,5-trimethoxybenzyl chloride are treated in the same manner as described in Example 1-(1) to give 3.7 g of 1-(3,4,5-trimethoxybenzyl)-1-(2-thienyl)propyl isocyanide as a colorless oil. yield; 67.5%

($cm^{-1}$): 2110

MS.(m/e): 349($M^+$)

(2) 3.7 g of 1-(3,4,5-trimethoxybenzyl)-1-(2-thienyl)propyl isocyanide are dissolved in 40 ml of methanol, and 5 ml of conc. hydrochloric acid are added to the solution. The mixture is stirred at 50°–60° C. for 2 hours. After the reaction, the mixture is evaporated to remove solvent and the residue (i.e., crude 1-(3,4,5-trimethoxybenzyl)-1-(2-thienyl)propylamine hydrochloride) is dissolved in a mixture of 30 ml of methanol and 2.5 g of 35% formalin. 1.84 g of sodium cyanoborohydride are added to the solution and the mixture is stirred at room temperature for 3 hours. After the reaction, the mixture is evaporated to remove solvent and 10% hydrochloric acid is added to the residue. The mixture is stirred for 15 minutes. After the reaction, the mixture is alkalized with potassium carbonate and extracted with ethyl acetate. The extract is washed with an aqueous saturated sodium chloride solution, dried and evaporated to remove solvent. The residue is purified by silica gel column chromatography (solvent; n-hexane:ethyl acetate=2:1) to give 1.8 g of 1-(3,4,5-trimethoxybenzyl)-1-(2-thienyl)-N,N-dimethylpropylamine as a colorless oil. yield; 46.2%

($cm^{-1}$): 1610, 1590

MS.(m/e): 349($M^+$)

NMR($CDCl_3$)δ:0.96(t, 3H), 1.6–1.9(m, 2H), 2.28(s, 6H), 3.09(s, 2H), 3.62, 3.73(s,s, 9H), 6.08(s, 2H), 6.7–7.2(m, 3H)

EXAMPLE 4

(1) 4.84 g of 1-(2-thienyl)propyl isocyanide and 6.87 g of 3-(3,4-dimethoxyphenyl)propyl chloride are treated in the same manner as described in Example 1-(1) to give 7.2 g of 1-ethyl-4-(3,4-dimethoxyphenyl)-1-(2-thienyl)butyl isocyanide as a colorless oil. Yield; 68.3%

($cm^{-1}$): 2120

MS.(m/e): 329($M^+$)

(2) 7.1 g of 1-ethyl-4-(3,4-dimethoxyphenyl)-1-(2-thienyl)butyl isocyanide are treated in the same manner as described in Example 3-(2) to give 3.77 g of 1-ethyl-4-(3,4-dimethoxyphenyl)-1-(2-thienyl)-N,N-dimethylbutylamine as a colorless oil. yield; 50.4%

($cm^{-1}$): 1610, 1590

MS.(m/e): 318($M^+$—$C_2H_5$)

NMR($CDCl_3$)δ0.98(t, 3H), 1.5–2.45(m, 6H), 2.63(s, 6H), 2.5–2.8(m, 2H), 3.82(s, 6H), 6.65–7.6(m, 6H)

Hydrochloride: colorless needles

M.p. 142°–143° C. (recrystallized from ethyl acetate)

EXAMPLE 5

(1) 5.44 g of 1-(2-thienyl)propyl isocyanide and 6.81 g of 3-(4-chlorophenyl)propyl chloride are treated in the same manner as described in Example 1-(1) to give 6.2 g of 1-ethyl-4-(4-chlorophenyl)-1-(2-thienyl)butyl isocyanide as a colorless oil. yield; 56.7%

($cm^{-1}$): 2120

MS.(m/e): 303($M^+$)

(2) 5.7 g of 1-ethyl-4-(4-chlorophenyl)-1-(2-thienyl)butyl isocyanide are treated in the same manner as described in Example 3-(2) to give 5.0 g of 1-ethyl-4-(4-chlorophenyl)-1-(2-thienyl)-N,N-dimethylbuthylamine as a colorless oil. yield; 83.9%

($cm^{-1}$): 1600, 1590

MS.(m/e): 321($M^+$)

NMR($CDCl_3$)δ: 0.80(t, 3H), 1.4–2.1(m, 6H), 2.12(s, 6H), 2.5–2.75(m, 2H), 6.7–7.35(m, 6H)

Maleate: colorless prisms

M.p. 118°–120° C. (recrystallized from ethyl acetate)

EXAMPLE 6

1.54 g of 62.5% sodium hydride (oily dispersion) are added to a solution of 4.96 g of thiocresol in 80 ml of toluene and the mixture is stirred at room temperature for 1 hour. 3.78 g of 1-ethyl-(3,4,5-trimethoxyphenyl)-1-(2-thienyl)-N,N-dimethylbutylamine are added to the mixture. 7 g of hexamethylphosphoric triamide are added dropwise to the mixture under ice-cooling and the mixture is refluxed for 18 hours. After cooling, the mixture is acidified with 10% hydrochloric acid. The aqueous layer is separated therefrom, adjusted to pH 8 with sodium bicarbonate and extracted with ethyl acetate. The extract is washed with an aqueous saturated sodium chloride solution, dried and evaporated to remove solvent. The residue is purified by silica gel column chromatography (solvent; n-hexane:ethyl acetate=1:1) to give 1.94 g of 1-ethyl-4-(4-hydroxy-3,5-dimethoxyphenyl)-1-(2-thienyl)-N,N-dimethylbutylamine as colorless crystals. yield; 53.4%

(cm$^{-1}$): 3350, 1610

MS.(m/e): 334(M+)

NMR(CDCl$_3$)δ:0.84(t, 3H), 1.4–2.2(m, 6H), 2.13(s, 6H), 2.57(t, 2H), 3.87(s, 6H), 5.1–5.6(broad s, 1H), 6.4(s, 2H), 6.75–7.30(m, 3H)

PREPARATION 1

(1) A mixture of 100 g of 2-propionylthiophene, 161 g of formamide and 98 g of formic acid is stirred at 150°–160° C. for 22 hours. After cooling, the mixture is poured into a solution of 30 g of potassium carbonate in 200 ml of water and extracted with ethyl acetate. The extract is washed, dried and evaporated to remove solvent. The residue is distilled under reduced pressure to give 96.5 g of 2-(1-formylaminopropyl) thiophene as a colorless oil. b.p. 154°–156° C./4 mmHg (cm$^{-1}$): 3250, 1660

(2) 231 g of triethylamine are added to a solution of 96.5 g of 2-(1-formylaminopropyl) thiophene in 500 ml of methylene chloride and the mixture is cooled at below −30° C. 105 g of phosphorus oxychloride are added dropwise to the mixture at below −30° to −20° C. and and the mixture is stirred at the same temperature for 1 hour. After the reaction, the mixture is poured into 1 litter of an aqueous 10% potassium carbonate solution. The aqueous mixture is stirred at room temperature for 1 hour and the methylene chloride layer is separated therefrom. Said methylene chloride layer is washed with water, dried and evaporated to remove solvent. The residue is distilled under reduced pressure to give 74.5 g of 1-(2-thienyl)propyl isocyanide as a colorless oil.

(cm$^{-1}$): 2150

What we claim is:

1. A thiophene derivative of the formula:

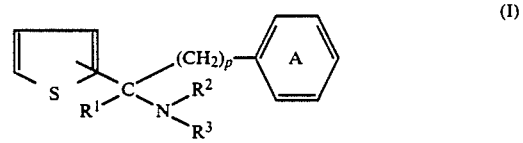

wherein $R^1$ is an ethyl group and $R^2$ and $R^3$ are a lower alkyl group, Ring A is a phenyl group, and p is an integer of 3, or a salt thereof.

2. The compound according to claim 1, which is 1-ethyl-4-phenyl-1-(2-thienyl)-N,N-dimethylbutylamine or a salt thereof.

3. A pharmaceutical composition which comprises a therapeutically effective amount of the compound claimed in claim 1 and a pharmaceutically acceptable carrier therefor.

4. A method of regulating gastrointestinal tract motility in a warm-blooded animal which comprises administering to said warm-blooded animal an effective amount of the compound according to claim 1.

5. A pharmaceutical composition which comprises a therapeutically effective amount of the compound claimed in claim 2 and a pharmaceutically acceptable carrier therefor.

6. A method of regulating a gastrointestinal tract motility in a warm-blooded animal which comprises administering to said warm-blooded animal an effective amount of the compound according to claim 2.

* * * * *